United States Patent [19]

Ladner et al.

[11] 4,404,402

[45] Sep. 13, 1983

[54] ANILINE INTERMEDIATES

[75] Inventors: David W. Ladner, Hamilton Square; Barrington Cross, Rocky Hill, both of N.J.

[73] Assignee: American Cyanamid Company, Stamford, Conn.

[21] Appl. No.: 354,682

[22] Filed: Mar. 4, 1982

Related U.S. Application Data

[63] Continuation of Ser. No. 179,340, Aug. 18, 1980, abandoned.

[51] Int. Cl.$^3$ .................. C07C 87/60; C07C 149/42; C07C 91/40; C07C 91/42
[52] U.S. Cl. .......................... 564/442; 71/76; 71/98; 71/103; 71/106; 71/114; 71/121; 564/305; 564/328; 564/440; 564/443; 564/412
[58] Field of Search ............... 564/305, 328, 440, 442, 564/443

[56] References Cited

U.S. PATENT DOCUMENTS

| | | | |
|---|---|---|---|
| 1,730,729 | 10/1929 | Hoffa et al. | 564/442 X |
| 2,056,899 | 10/1936 | Hoffa et al. | 564/442 |
| 2,971,953 | 2/1961 | Rhyner | 564/440 X |
| 3,192,199 | 6/1965 | McMillan et al. | 564/328 X |
| 3,726,662 | 4/1973 | Howe et al. | 71/103 |
| 4,145,364 | 3/1979 | Mulvey et al. | 564/442 X |

FOREIGN PATENT DOCUMENTS

| | | | |
|---|---|---|---|
| 54-122232 | 9/1979 | Japan | 71/103 |
| 895395 | 5/1962 | United Kingdom | 564/305 |

OTHER PUBLICATIONS

Bursey et al., "J. Org. Chem.", vol. 36, No. 1, pp. 137–140, (1971).
Godfrey et al., "J. Chem. Soc. (C)", pp. 400–404, (1967).

*Primary Examiner*—John Doll
*Attorney, Agent, or Firm*—Thomas J. Monahan

[57] ABSTRACT

There are provided novel substituted aniline intermediates, useful in the synthesis of certain substituted N-nitroanilines or salts thereof which may be used to elicit several desirable and advantageous biological responses in plants.

1 Claim, No Drawings

ANILINE INTERMEDIATES

This is a continuation, of application Ser. No. 179,340, filed Aug. 18, 1980 presently abandoned.

The invention is substituted anilines of Formula (I):

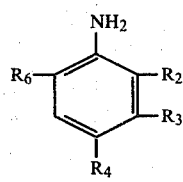

wherein $R_2$ is Br, Cl, F, I, $CH_3$, $CF_3$, CN, $SO_2F$, $OCHF_2$, $OCH_3$, $SO_2H$, $CH_3SO_2$, $C_3H_7$-i, $SO_2C_6H_5$, $SO_2 C_4H_9$, $SCH_3$, CO $C_6H_5$ or $COCH_3$; $R_3$ is H, $CH_3$, Br, Cl, F or $SO_2CH_3$, $R_4$ is H, Br, Cl, F, $OCF_3$, $SO_2$ $C_6H_5$, CO $C_6H_5$ or $SO_3$ $CH_2$ $C_6H_5$; $R_6$ is Br, Cl, F, I or $C_3H_7$-i.

The above-described compounds of Formula (I) are valuable intermediates for the preparation of certain substituted N-nitroanilines useful for enhancing axillary branching, dwarfing, stem stiffening, canopy, flowering and crop yield of plants and as lodging inhibitors therefor. These plant regulating N-nitroanilines may be graphically represented by Formulae II or IIa or mixtures thereof or salts thereof as represented by Formula (III):

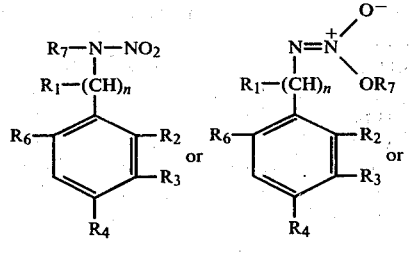

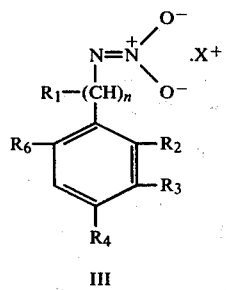

wherein n is an integer of 0 or 1; the groups from $R_1$ to $R_7$ represent various substituents including those of the compounds represented by Formula (I) above; cation $X^+$ is inorganic or organic. The compounds of Formulae II, IIa or III are disclosed and described in U.S. Pat. No. 4,367,339, and incorporated herein by way of reference.

Of special interest are compounds of Formula (I) of the invention wherein $R_4$ and $R_6$ are both Br; $R_2$ is $CF_3$, CN, $SO_2F$, $OCHF_2$, $OCH_3$, $SO_2H$, $CH_3SO_2$, $C_3H_7$-i, $SO_2 C_6H_5$, $SO_2 C_4H_9$, $SCH_3$, $COCH_3$ or $COC_6H_5$; $R_3$ is H.

A valuable group of compounds of the invention are those wherein $R_2$ and $R_6$ are both Br; $R_3$ is H; $R_4$ is $SO_2 C_6H_5$, $COC_6H_5$, $SO_3CH_2C_6H_5$ or $OCF_3$.

Another useful group of compounds of interest are those wherein $R_2$, $R_4$ and $R_6$ are Br, and $R_3$ is $SO_2 CH_3$ or F.

A further group of compounds of Formula I and of interest are those wherein $R_3$ is Cl; $R_6$ is Br; $R_2$ and $R_4$ are substituted in the following combinations

| $R_2$ | $R_4$ |
|---|---|
| Br | Cl |
| $CH_3$ | Br |
| Br | $CH_3$ |

Also of interest are those compounds wherein when $R_2$ is Br, then $R_6$ is I, Cl or F, and when $R_2$ is Cl, then $R_6$ is I or F.

The following compounds of the invention are also of value:
2,4,6-triiodoaniline;
4-bromo-2,6-diisopropylaniline,
and
2,3,6-tribromoaniline.

Conveniently, the compounds of the invention may be prepared by a number of methods, as illustrated in the following:

METHOD A

A solution of bromine in glacial acetic acid is added to a solution of the appropriately substituted aniline in glacial acetic acid in a 1:1 molar ratio at below 25° C. and the reaction mixture agitated until the reaction is essentially complete. The product is precipitated with water, isolated and purified if so desired by standard laboratory procedures.

METHOD B

A solution of the appropriately substituted aniline in methylene chloride is treated with excess amounts of bromine in the presence of sodium bicarbonate in the temperature range of −60° to −70° C. for a period of time sufficient to essentially complete the reaction. The product is then isolated by standard laboratory procedures and further purified if so desired.

METHOD C

Preparation of anilines substituted with alkylsulfonyl groups.

The appropriately substituted fluorosulfonylaniline is reacted with the appropriate alkyllithium compound in an inert solvent such as ether under a nitrogen atmosphere at a temperature range of −60° to −70° C. The reaction mixture is then warmed to room temperature, poured into ice and the product isolated from the organic layer by standard laboratory procedures.

METHOD D

Anilines containing fluorosulfonyl groups may be reduced to the corresponding sulfinic acids with excess sodium sulfite in an aqueous medium in the temperature range of 60° to 80° C. The product is isolated from the reaction mixture by standard laboratory procedures.

METHOD E

A solution of 4-chloroaniline in aqueous hydrochloric acid when treated with excess iodine monochloride under a nitrogen atmosphere yields the corresponding 2,6-diiodo derivative.

METHOD F

Treating the appropriately substituted aniline with N-bromosuccinimide in the presence of an inert solvent at about −60° to −70° C. affords the corresponding bromo derivative.

METHOD G

The sulfinic acids obtained by Method D above may be converted to the corresponding difuloromethylsulfonyl derivative with chlorodifluoromethane in the presence of a lower alcohol, water and a base such as sodium hydroxide.

As stated above, the Formula (I) compounds of the present invention are valuable intermediates for the preparation of plant regulating N-nitroanilines. These N-nitroanilines (phenylnitramines) may be prepared from said anilines by a variety of conventional procedures. For illustrative purposes, one such procedure is graphically illustrated and described as follows:

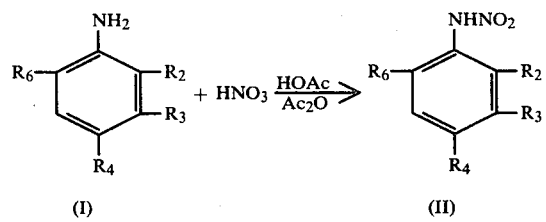

(I)        (II)

wherein $R_2$ to $R_6$ are defined above. The above synthesis is conveniently carried out in a solvent such as acetic acid, preferably in the presence of acetic anhydride. The product may be precipitated from the reaction mixture by the addition of ice water. Purification may be effected by conventional procedures such as recrystallization, chromatography and the like.

The salts of Formula II substituted N-nitroanilines may be prepared by a variety of conventional procedures. For illustrative purpose, one such procedure is described as follows:

The N-nitroaniline is dissolved in dilute aqueous sodium or potassium hydroxide and filtered. To this solution is added one molar equivalent of the appropriate amine salt dissolved in water. In most cases the product separates as a solid, and is removed by filtration and purified by recrystallization. Whenever no precipitation occurs or the product separates as an oil, an extraction with methylene chloride is performed. Concentration of this extract yields the product which may be further purified by recrystallization.

In practice, application to the foliage of seedling plants of from about 0.06 to 2.0 kg/ha of a phenylnitramine or a salt thereof is sufficient to achieve the several desirable and advantageous biological responses in plants referred to above.

The invention is further illustrated by the examples set forth below which are not intended to be limiting on the invention.

EXAMPLE 1

PREPARATION OF SUBSTITUTED ANILINES

METHOD A

Preparation of 2-bromo-4,6-difluoroaniline.

A solution of bromine (16.0 g; 0.10 mol) in glacial acetic acid (25 ml) is added dropwise to a solution of 2,4-difluoroaniline (12.9 g; 0.10 mol) in glacial acetic acid (75 ml) while maintaining the temperature of the reaction mixture below 25° C. The reaction mixture is stirred an additional 0.5 hour during which time a solution of sodium acetate (5.48 g; 0.137 mol) in water (100 ml) is added. The reaction mixture is then diluted with water (300 ml), the precipitated purple solid is filtered, washed with water (100 ml) and dried under vacuum.

Recrystallization of the solids from aqueous ethanol affords 14.14 g of product, m.p. 40°–42° C. (yield: 68%).

METHOD B

Preparation of 2,6-dibromo-4-phenoxyaniline.

A solution of 4-phenoxyaniline (2.0 g; 0.0108 mol) in methylene chloride (50 ml) is chilled to −65° C., sodium bicarbonate (1.99 g; 0.0237 mol) is added and the mixture stirred for 10 minutes. A solution of bromine (3.792 g; 0.0237 mol) in methylene chloride is added dropwise at −65° C. On completion of the addition, the reaction mixture is stirred for 45 minutes, poured into water and extracted with ethylene chloride. The organic extracts are dried and evaporated under vacuum. The residue is purified by chromatography (silica gel column; eluent:hexane:ethyl acetate:95:5) to afford the product.

METHOD C

Preparation of 2,4-dibromo-6-(methylsulfonyl)aniline.

A solution of 2-fluorosulfonyl-4,6-dibromoaniline (7.19 g; 0.0216 mol) in ether (100 ml) is cooled to −65° C. under a nitrogen atmosphere and a solution of methyllithium in ether (37.5 ml of 1.8 M; 0.0675 mol) is added via a syringe. The mixture is allowed to warm to 0° C., the solution is poured into ice, and the ether layer is separated. The aqueous layer is extracted with ether (3×100 ml) and the ether layers are combined. The solvent is removed under reduced pressure and the residue crystallized from petroleum ether to afford the title product.

METHOD D

Preparation of 2-amino-3,5-dibromobenzenesulfinic acid.

A mixture of sodium sulfite ($Na_2SO_3$; 20.2 g; 0.16 mol) and water (100 ml) is stirred and heated to 70° C. and 2-fluorosulfonyl-4,6-dibromoaniline (13.3 g; 0.04 mol) is added at once. The reaction mixture cools down somewhat and is reheated to 70° C. and maintained at that temperature for 20 hours. The reaction mixture is then cooled down, acidifed with 10% hydrochloric acid to yield a white precipitate. The precipitate is filtered, washed with water and dried to afford 10 g of title product, m.p. 112° C. (decomposed).

Analysis

Calculated for: $C_6H_5Br_2NO_2S$: C 22.88; H 1.60; N, 4.45; S 10.18; Br 50.74.

Found: C 22.69; H 1.58; N 4.36; S 9.89; Br 50.58.

METHOD E

Preparation of 4-chloro-2,6-diiodoaniline.

A solution of 4-chloroaniline (6.9 g; 0.0537 mol) in aqueous hydrochloric acid (500 ml HCl/3500 ml $H_2O$) is treated with iodine monochloride (ICl; 35.1 g; 0.216 mol) under a stream of nitrogen for about 12 hours. The resulting precipitate is filtered, washed with water (300 ml) and dried under vacuum. The crude is recrystallized from aqueous ethanol to afford 16.1 g of title product, m.p. 127°–129° C.

METHOD F

Bromination of 2,3-dimethylaniline.

A solution of 2,3-dimethylaniline (100 g; 0.826 mol) in toluene is cooled to −72° C. and then about one half of the required NBS (147 g; 0.826 mol) is added at once. The reaction mixture exotherms to −65° C. Next, 100 ml of toluene and the rest of the above NBS is added. Further exotherm took place. When the reaction mixture cooled down to −70° C., the cooling bath is removed and the reaction mixture is allowed to warm up to room temperature overnight under the exclusion of light. The precipitated succinimide is filtered off, the solution cooled in an ice bath and acetic anhydride added (47 ml; 0.495 mol). The reaction mixture is stirred for 2 hours, filtered, the solids washed with toluene and dried and then recrystallized from isopropyl alcohol to afford 29.8 g of 4-bromo-2,3-dimethylacetanilide m.p. 148°–151° C.

The above solution is extracted with dilute hydrochloric acid, the aqueous extract is made alkaline and the precipitated material is distilled to afford 18.2 g of 2-bromo-5,6-dimethylaniline, bp. 84° C. at 0.05 mm.

METHOD G

Preparation of 2,4-dibromo-6-[(difluoromethyl)sulfonyl]aniline.

A solution of 2-amino-3,5-dibromobenzenesulfinic acid (7.98 g; 0.025 mol) in a mixture of isopropyl alcohol (100 ml) and sodium hydroxide (8.0 g of 50% aqueous) and water (2 ml) is warmed to 40° C. Chlorodifluoromethane is added slowly through a gas inlet tube over a period of 3 hours. The reaction mixture exotherms to 55° C. The reaction mixture is poured into water (500 ml) and the solution is extracted with methylene chloride (2×100 ml). The combined extracts are washed with saturated NaHCO$_3$ (100 ml), saturated NaCl (100 ml), then dried over MgSO$_4$. The solvent is evaporated under vacuum yield 0.9 g of the title product, m.p. 84°–88° C.

By one or the other method discussed above, a number of anilines are prepared. These are listed in Table I below.

TABLE I

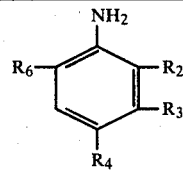

| No. | Method | R$_2$ | R$_3$ | R$_4$ | R$_6$ | mp °C. |
|---|---|---|---|---|---|---|
| 1 | A | CF$_3$ | H | Br | Br | 42–44 |
| 2 | A | CN | H | Br | Br | 151–152.5 |
| 3 | A | SO$_2$F | H | Br | Br | 56–60 |
| 4 | G | OCHF$_2$ | H | Br | Br | 45–46 |
| 5 | C | SO$_2$CH$_3$ | H | Br | Br | 121–124 |
| 6 | D | SO$_2$H | H | Br | Br | 112 |
| 7 | B | OCH$_3$ | H | Br | Br | 110 |
| 8 | A | i-C$_3$H$_7$ | H | Br | Br | 177–193 |

TABLE I-continued

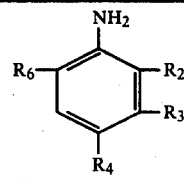

| No. | Method | R$_2$ | R$_3$ | R$_4$ | R$_6$ | mp °C. |
|---|---|---|---|---|---|---|
| 9 | E | I | H | F | I | 99–100 |
| 10 | C | SO$_2$C$_6$H$_5$ | H | Br | Br | 161–162 |
| 11 | C | SO$_2$C$_4$H$_9$—n | H | Br | Br | |
| 12 | A | Br | H | SO$_2$C$_6$H$_5$ | Br | |
| 13 | B | SCH$_3$ | H | Br | Br | oil |
| 14 | A | COCH$_3$ | H | Br | Br | 121.5–122.5 |
| 15 | A | Br | H | —C(O)—C$_6$H$_5$ | Br | 146.5–147 |
| 16 | A | —C(O)—C$_6$H$_5$ | H | Br | Br | 98–98.5 |
| 17 | A | Br | H | OCF$_3$ | Br | |
| 18 | | Br | H | SO$_2$CH$_2$C$_6$H$_5$ | Br | |
| 19 | | Br | H | C$_6$H$_5$O | Br | |
| 20 | A | Br | Cl | Cl | Br | 110 |
| 21 | A | Br | Cl | CH$_3$ | Br | 78 |
| 22 | A | CH$_3$ | Cl | Br | Br | 68.5–70 |
| 23 | F | Br | Br | H | Br | |
| 24 | | Br | F | Br | Br | 98 |
| 25 | | Br | SO$_2$CH$_3$ | Br | Br | |
| 26 | | Br | H | H | I | |
| 27 | | Br | H | H | Cl | |
| 28 | | Cl | H | H | I | |
| 29 | | CH$_3$ | CH$_3$ | H | Br | oil, bp. 55–84° C./0.05 mm |

EXAMPLE 2

EVALUATION OF SUBSTITUTED N-NITROANILINE SALTS AS DWARFING AND STEM STIFFENING AGENTS FOR SOYBEANS

In the following tests, test compounds are dissolved or dispersed in acetone-water (1:1) mixtures at the final concentration corresponding to the kg/ha rates indicated in the table below. The solution also contains 0.25% v/v colloidal BIOFILM ® (a product of Colloidal Products Corp.) which is a mixture of alkyl aryl polyethoxyethanol, free and combined fatty acids, glycol ethers, dialkylbenzene carboxylate and 2-propanol.

The plant species used in these tests are soybeans (*Glycine max*)Adelphia.

The solution or dispersion of the compound under test is sprayed at a rate of 747 l/ha with a moving nozzle along an overhead stationary track. The spray nozzle moves at a constant speed over the plants.

The plants are grown in plastic pots and are well established at the time of treatment. The seedlings of soybeans are at the second to third trifoliate stage. Plants are watered prior to treatment and then sprayed to provide the kg/ha rate of test compound desired.

After spraying the plants are placed on greenhouse benches and watered and fertilized in accordance with normal greenhouse procedures.

Three weeks after spraying the plants are measured and harvested. All treatments are replicated six times and comparisons are made against untreated controls. Data obtained are reported in Table II below as percent reduction in plant height over untreated controls.

TABLE II

| Compound | Rate kg/ha | % Reduction in Plant Height over untreated controls |
|---|---|---|
| 1,2-Dimethyl-3,5-di- phenlypyrazolium salt with 4,6-dibromo- α, α, α-trifluoro-N— aci-nitro-o-toluidine | 0.5 0.25 0.125 | >40 >40 >20 |
| 1,2-Dimethyl-3,5-di- phenylpyrazolium salt with 2,6-dibromo-4- chloro-N—aci-nitro- aniline | 0.5 0.25 0.125 | >40 >30 >25 |
| 1,2-Dimethyl-3,5-di- phenylpyrazolium salt with 2,4-dibromo-6- ioda-N—aci-nitro- aniline | 0.5 0.25 0.125 | >25 >15 >10 |

We claim:

1. A compound having the following structural formula:

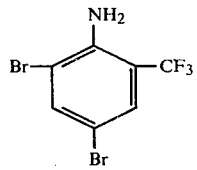

* * * * *